United States Patent
Jimenez et al.

(10) Patent No.: US 9,974,927 B2
(45) Date of Patent: May 22, 2018

(54) CATHETER WITH FLAT BEAM DEFLECTION IN TIP

(71) Applicant: BIOSENSE WEBSTER (ISRAEL) LTD., Yokneam (IL)

(72) Inventors: Jose Jimenez, Ontario, CA (US); Ricardo Padilla, Tustin, CA (US); Thomas V. Selkee, Claremont, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days. days.

(21) Appl. No.: 15/256,490

(22) Filed: Sep. 2, 2016

(65) Prior Publication Data
US 2016/0367788 A1    Dec. 22, 2016

Related U.S. Application Data

(62) Division of application No. 13/677,214, filed on Nov. 14, 2012, now Pat. No. 9,433,752.

(51) Int. Cl.
*A61M 31/00*    (2006.01)
*A61M 37/00*    (2006.01)
(Continued)

(52) U.S. Cl.
CPC .... *A61M 25/0147* (2013.01); *A61M 25/0009* (2013.01); *A61M 25/0026* (2013.01);
(Continued)

(58) Field of Classification Search
CPC .......... A61M 25/0052; A61M 25/0054; A61M 25/0147; A61M 25/0141; A61M 25/0144;
(Continued)

(56) References Cited

U.S. PATENT DOCUMENTS 4,886,067 A    12/1989 Palermo
5,203,772 A    4/1993 Hammerslag et al.
(Continued)

FOREIGN PATENT DOCUMENTS

CN    101896217 A    11/2010
CN    102159278 A    8/2011
(Continued)

OTHER PUBLICATIONS

European Patent Office Action dated Feb. 19, 2014, in EP Application No. 13192776, 8 pages.

*Primary Examiner* — Imani Hayman
*Assistant Examiner* — Tiffany Legette-Thompson
(74) *Attorney, Agent, or Firm* — Roberts Mlotkowski Safran Cole & Calderon, P.C.

(57) ABSTRACT

A catheter has a deflection beam with rectangular cross-section and a single continuous puller wire for predictable on-plane bi-directional deflection. The puller wire extends through spacers on opposite sides of the beam so the puller wire is maintained a predetermined separation distance from the beam surface. Tubular structures of the catheter body and the deflectable section are fused at a joint by C-shaped brackets mounted opposite surface of the beam to form a hollow body with holes into which thermoplastic materials covering the catheter body and the deflectable section can melt to form interlocking nodes. Elongated beam stiffeners can be mounted on the beam to provide different curve and deflection geometries.

2 Claims, 14 Drawing Sheets

(51) Int. Cl.
  *A61M 25/01* (2006.01)
  *B29C 63/00* (2006.01)
  *B29C 63/18* (2006.01)
  *B29C 65/02* (2006.01)
  *A61M 25/00* (2006.01)
  *A61B 18/14* (2006.01)
  *B29L 31/00* (2006.01)

(52) U.S. Cl.
  CPC .... *A61M 25/0138* (2013.01); *A61M 25/0141* (2013.01); *A61M 25/0144* (2013.01); *B29C 63/0069* (2013.01); *B29C 63/18* (2013.01); *B29C 65/02* (2013.01); *A61B 18/1492* (2013.01); *A61M 25/0051* (2013.01); *A61M 25/0052* (2013.01); *A61M 2025/015* (2013.01); *A61M 2207/00* (2013.01); *B29K 2995/0049* (2013.01); *B29L 2031/7542* (2013.01)

(58) Field of Classification Search
  CPC .......... A61M 25/0051; A61B 18/1492; A61B 2018/00839; A61B 2218/002
  USPC ................................. 604/95.04, 524
  See application file for complete search history.

(56) References Cited

U.S. PATENT DOCUMENTS

| | | | |
|---|---|---|---|
| RE34,502 E | 1/1994 | Webster, Jr. | |
| 5,358,479 A | 10/1994 | Wilson | |
| 5,562,619 A | 10/1996 | Mirarchi et al. | |
| 5,782,828 A | 7/1998 | Chen et al. | |
| 5,807,249 A | 9/1998 | Qin et al. | |
| 5,984,907 A | 11/1999 | McGee et al. | |
| 6,033,378 A | 3/2000 | Lundquist et al. | |
| 6,287,301 B1 | 9/2001 | Thompson et al. | |
| 6,554,794 B1 | 4/2003 | Mueller et al. | |
| 6,585,717 B1 | 7/2003 | Wittenberger et al. | |
| 6,890,329 B2 | 5/2005 | Carroll et al. | |
| 6,926,711 B2 | 8/2005 | Lentz et al. | |
| 7,008,401 B2 | 3/2006 | Thompson et al. | |
| 7,141,024 B2 | 11/2006 | Gaber | |
| 7,232,422 B2 | 6/2007 | Gibson et al. | |
| 7,588,555 B2 | 9/2009 | Pudelko et al. | |
| 2001/0041891 A1 | 11/2001 | Thompson et al. | |
| 2002/0068868 A1 | 6/2002 | Thompson et al. | |
| 2002/0082585 A1 | 6/2002 | Carroll et al. | |
| 2002/0165461 A1* | 11/2002 | Hayzelden | A61B 18/1492 600/523 |
| 2003/0181855 A1* | 9/2003 | Simpson | A61M 25/0041 604/95.04 |
| 2004/0230178 A1* | 11/2004 | Wu | A61B 17/320725 604/527 |
| 2006/0184106 A1* | 8/2006 | McDaniel | A61B 18/1492 604/95.04 |
| 2012/0123327 A1 | 5/2012 | Miller | |

FOREIGN PATENT DOCUMENTS

| | | |
|---|---|---|
| EP | 1690564 A1 | 8/2006 |
| JP | H07505554 A | 6/1995 |
| JP | 2006-255401 A | 9/2006 |
| JP | 2010-75530 A | 4/2010 |
| JP | 2012-100829 A | 5/2012 |
| WO | 2010035599 A1 | 4/2010 |

* cited by examiner

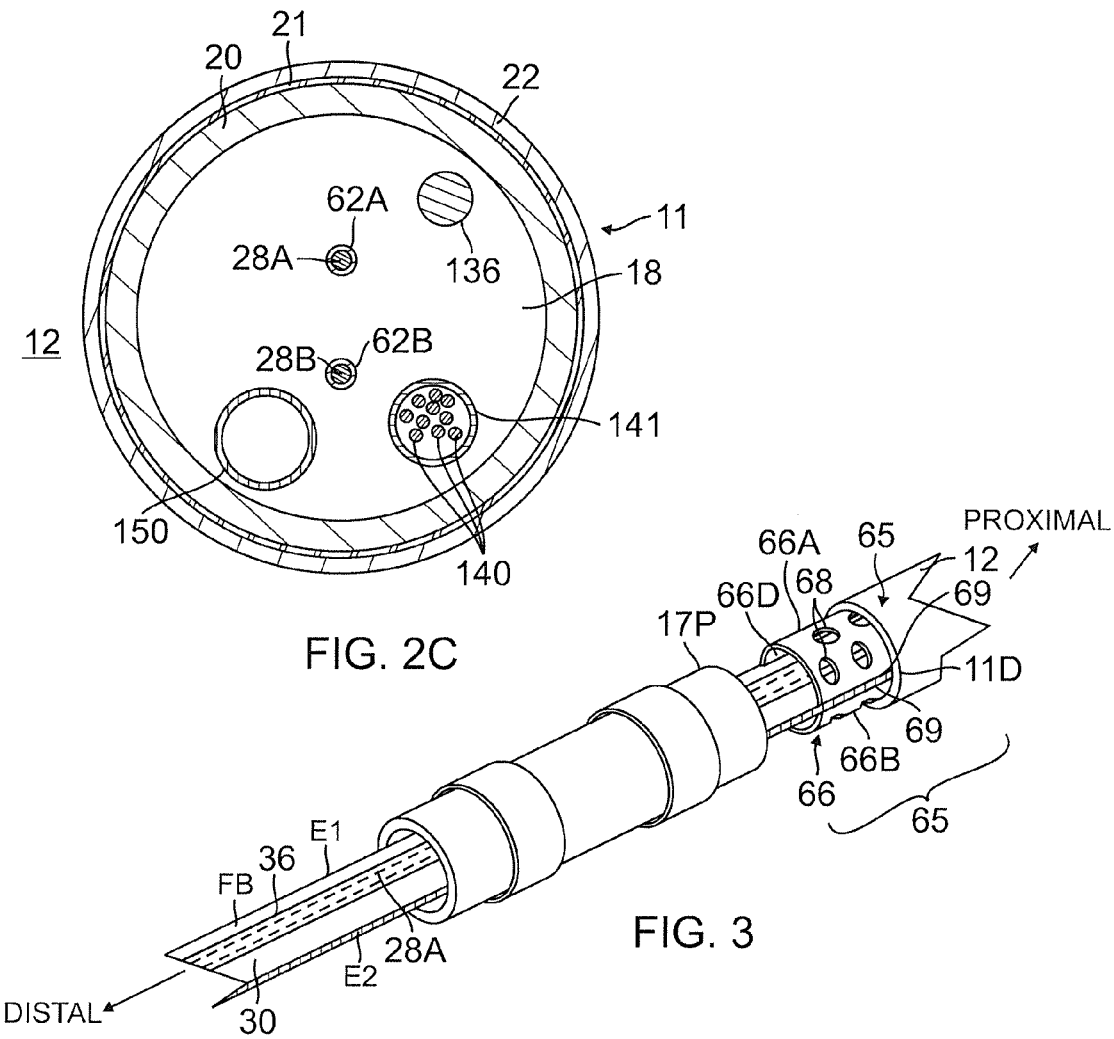
FIG. 2C
FIG. 3
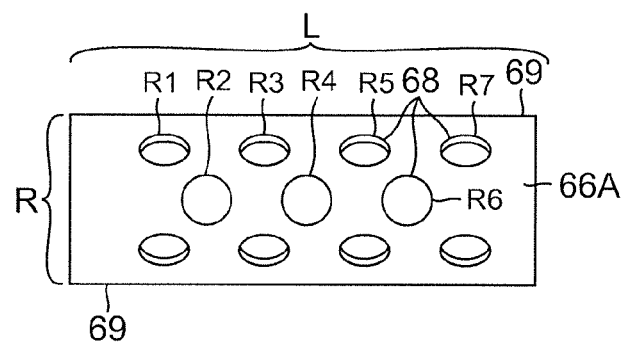
FIG. 3A

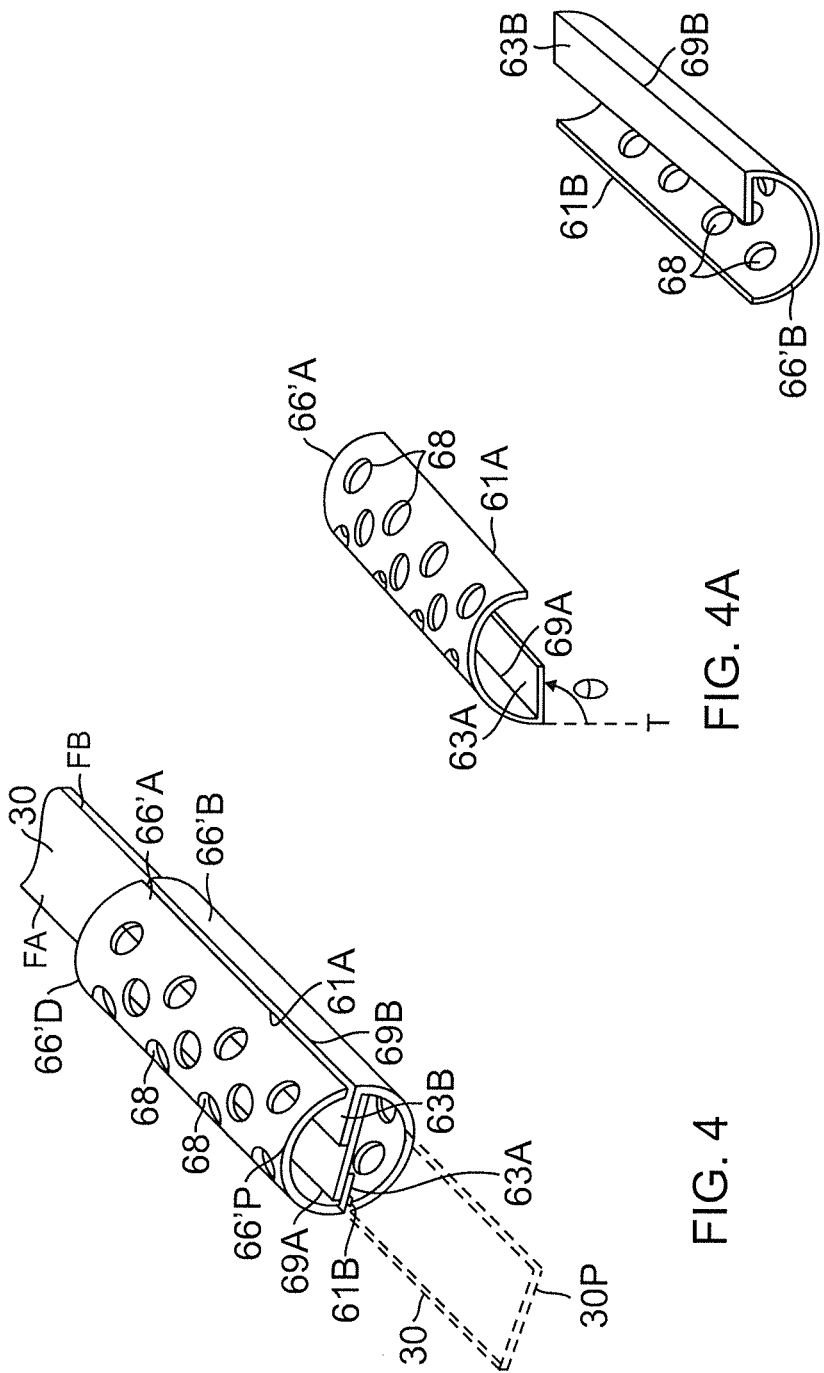

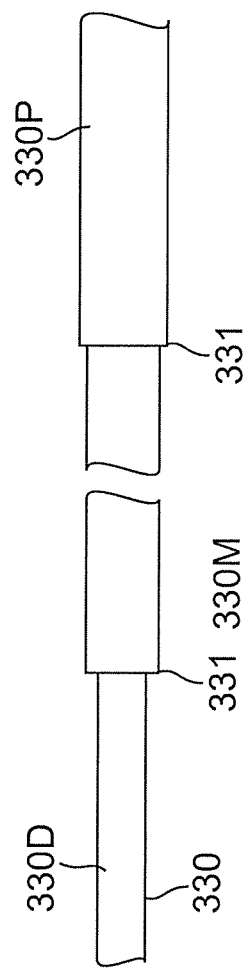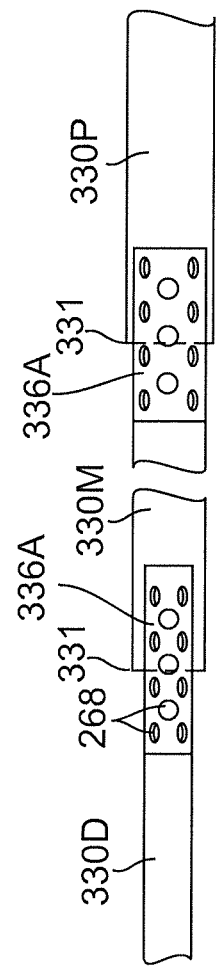
FIG. 12
FIG. 12 A

CATHETER WITH FLAT BEAM DEFLECTION IN TIP

CROSS-REFERENCE TO RELATED APPLICATION

This application is a divisional application of and claims priority to and the benefit of U.S. patent application Ser. No. 13/677,214 filed Nov. 14, 2012, issued as U.S. Pat. No. 9,433,752, the entire content of which is incorporated herein by reference.

FIELD OF INVENTION

The present invention relates to a medical device for use in the vessel of a patient for the purpose of diagnosing or treating the patient, such as mapping tissue and/or ablating tissue using radio frequency (RF) or other sources of energy. More particularly, the invention relates to a deflectable catheter having a flat beam for on-plane bi-directional deflection.

BACKGROUND

Electrode catheters have been in common use in medical practice for many years. They are used to stimulate and map electrical activity in the heart and to ablate sites of aberrant electrical activity. Atrial fibrillation is a common sustained cardiac arrhythmia and a major cause of stroke. This condition is perpetuated by reentrant wavelets propagating in an abnormal atrial-tissue substrate. Various approaches have been developed to interrupt wavelets, including surgical or catheter-mediated atriotomy. Prior to treating the condition, one has to first determine the location of the wavelets. Various techniques have been proposed for making such a determination, including the use of catheters with a mapping assembly that is adapted to measure activity within a pulmonary vein, coronary sinus or other tubular structure about the inner circumference of the structure. One such mapping assembly has a tubular structure comprising a generally circular main region generally transverse and distal to the catheter body and having an outer circumference and a generally straight distal region distal to the main region. The tubular structure comprises a non-conductive cover over at least the main region of the mapping assembly. A support member having shape-memory is disposed within at least the main region of the mapping assembly. A plurality of electrode pairs, each comprising two ring electrodes, are carried by the generally circular main region of the mapping assembly.

In use, the electrode catheter is inserted into a guiding sheath which has been positioned a major vein or artery, e.g., femoral artery, and guided into a chamber of the heart. Within the chamber, the catheter is extended past a distal end of the guiding sheath to expose the mapping assembly. The catheter is maneuvered through movements so that the mapping assembly is positioned at the tubular region in the heart chamber. The ability to control the exact position and orientation of the catheter is critical and largely determines how useful the catheter is.

Steerable catheters are generally well-known. For example, U.S. Pat. No. Re 34,502 describes a catheter having a control handle comprising a housing having a piston chamber at its distal end. A piston is mounted in the piston chamber and is afforded lengthwise movement. The proximal end of the elongated catheter body is attached to the piston. A puller wire is attached to the housing and extends through the piston, through the catheter body, and into a tip section at the distal end of the catheter body. In this arrangement, lengthwise movement of the piston relative to the housing results in deflection of the catheter tip section.

The design described in U.S. Pat. No. RE 34,502 is generally limited to a catheter having a single puller wire. If bi-directional deflection is desire, more than one puller wire becomes necessary. Catheters adapted for on-plane bi-directional deflection are also known. A flat beam is normally provided to enable deflection on both sides of the beam sweeping a defined plane. However, the puller wire in tension under deflection often flips over to the other side of the beam, or where the puller wires are located close to the beam, a large bending moment is required to deflect the beam, imposing significant stress on the puller wires. Moreover, with the puller wires close and tightly constrained to the beam, adhesion failure or rupture of the puller wire from the beam poses a significant risk of injury to the patient.

The employment of a pair of puller wires to effectuate bi-directional deflection also required a number of components that occupy space in a space-constrained catheter. More components also increased the risk of component failures. The use of T-bars and/or crimps can unduly fatigue puller wires and impart shear stresses resulting from skewed or off-axis alignment of puller wires relative to the longitudinal axis of the catheter, even if by a minor degree.

Moreover, tubular regions of the heart can vary greatly in size. A catheter of a uniform width along its length may not be well adapted for use in such tubular regions. For example, a deflectable tip with a larger french size may impede cannulation and tracking in a smaller tubular region and a deflectable tip with a smaller French size may not be stable in a larger tubular region. Moreover, in particular regions of the heart, different deflection and stiffness may be required.

Flat beam construction also requires a method to construct a joint between the catheter body and the deflectable section in a manner that provides support and endurance for torsional and axial loads placed on the joint in a clinical environment. Abutting ends of tubings covering the beam at the joint may separate and detach from each other due to excessive torsional or axial forces. Any underlying joint support structure should facilitate bonding of the tubings.

Thus, there is a desire for a catheter with more deflection variety and options, including a deflectable section that employs a puller wire configuration that improves durability while facilitating ease in deflection. There is also a desire for a catheter to have a tapered profile with a wider proximal end and a narrower distal end and a joint between the catheter body and deflection section that can provide sufficient torsional stiffness and withstand significant torsional and axial load.

SUMMARY OF THE INVENTION

The present invention is directed to a catheter having a deflection beam and a single continuous puller wire to effectuate predictable on-plane bi-directional deflection with less deflection components for reducing catheter size without compromising functionality, including the ability to carry, house and support mapping and/or ablation components, such as a multitude of electrodes and lead wires. The catheter includes an elongated catheter body, a deflectable section, a distal assembly carrying diagnostic and/or therapeutic electrodes, and a control handle. For bi-directional deflection, the deflection beam of the deflectable section has a rectangular cross section with first and second opposing surfaces defining corresponding first and second opposing directions of deflection. Acting on the deflection beam, the single continuous puller wire has a U-bend at or near a midpoint of the wire, which is anchored at a distal end of the deflection beam. Extending proximally therefrom are first and second proximal segments of the puller wire which extend in parallel with the deflection beam through the deflectable section on opposite sides of the beam along the first and second surfaces, respectively. The first and second proximal segments further extend proximally through the catheter body and into the control handle where proximal ends of the puller wire are anchored. To minimize the force required to bend the deflection beam, each proximal segment extending along the deflection beam is guided, maintained and/or bounded to the beam at a predetermined separation distance from the beam surface by a spacer. The spacers also increase durability of the puller wires by providing a geometry that allows tensile load with minimal shear stress.

Tubular structures of the catheter body and the deflectable section are fused at a joint for exceptional torsional coupling. The joint includes a pair of brackets mounted at or near a proximal end of the deflection beam at a transition between the catheter body and the deflectable section. The pair of brackets, each mounted on an opposite surface of the beam, jointly form a hollow body circumferentially surrounding the beam which supports abutting ends of the tubular structures that are slipped over distal and proximal ends of the hollow body. Advantageously, the hollow body allows lead wires, cables and tubings to pass through the joint without interruption, while providing support to the tubular structures of the catheter body and the deflectable section Moreover, each bracket has holes for receiving interlocking fused nodes formed from melted inner layers of each tubular structure during the application of heat and pressure, for example, by utilizing a two piece thermal fusing die.

Each bracket may have a curved body in the shape of a half-cylinder with a "C" cross section with two lengthwise edges that are affixed to a side of the beam. Alternatively, each bracket may have a curved body in the shape of a half-cylinder with an angled rectangular planar portion adjoined thereto, forming a "G" cross-section, with the planar portion being affixed to a side of the beam and the lengthwise edge being unattached and free floating. In the latter embodiment, the partially attached half-cylinder body acts as a spring to provide an outward pressure against the inner layers of the tubular structures during fusion under heat and pressure to facilitate the formation of the interlocking nodes.

The beam may have a constant width along its length, or the width may taper and be narrowed from the proximal end to the distal end so that the deflectable section has a tapered profile, enabling the wider proximal end to have better anchoring in larger tubular regions of the patient's body and the narrower distal end to have better maneuverability in smaller tubular regions. The tapering may occur gradually, smoothly and in a linear fashion with no sharp corners, or the tapering may occur in a nonlinear fashion with steps and corners. In any event, the brackets mounted on the beam have a corresponding shape, including a corresponding width or diameter that matches the width dimension of the beam at the locations of the brackets, so as to effectively support the tubular structures covering the beam.

The beam may also be adapted for different curve and deflection geometries by the use of one or more elongated beam stiffeners. The stiffeners may have different widths and lengths relative to each other and/or to the beam. They may be affixed to the beam on one or both surfaces of the beam. They may be affixed continuously along their lengths, e.g., by adhesives, or at selected locations, e.g., by resistance spot welding, brazing or laser welding methods. They may also be affixed to the beam solely at their or near their proximal ends, depending on the curve and deflection desired.

In one embodiment, a catheter of the present invention includes an elongated catheter body with a first tubular structure having first central lumen, and a deflectable section having a second tubular structure with a second central lumen and a flat beam extending therethrough where the beam divides the second central lumen into a first sub-lumen and a second sub-lumen. The catheter includes a puller wire configured with parallel first and second segments connected by a U-bend segment, where the U-bend segment is anchored to the distal end of the flat beam, the first segment extends through the first sub-lumen of the deflectable section and the central lumen of the catheter body, and the second segment extends through the second sub-lumen of the deflectable section and the central lumen of the catheter body. The catheter also includes a compression coil for each of the first and second segments extending through the catheter body, where each compression coil has a distal end at or near the distal end of the catheter body so that effectuate deflection initiates distal of the catheter body. The catheter further includes a pair of first and second brackets, each mounted on a respective surface of the beam to jointly form a hollow body generally surrounding the beam at or near a joint between the catheter body and the deflectable section, where a distal end of the catheter body covers a proximal portion of the hollow body and a proximal end of the deflectable section covers a distal portion of the hollow body.

In a more detailed embodiment, each half-cylindrical bracket has a C cross section and the pair of first and second brackets form a generally cylindrical hollow body surrounding the beam. Each bracket has a plurality of holes configured to receive interlocking nodes extending from inner surfaces of the tubular structures covering the hollow body.

In another more detailed embodiment, the spacer includes an adhesive layer applied to each surface of the beam and a tubing affixed to the adhesive layer where the tubing has a lumen through which the puller wire extends. The layer and a wall of the tubing provide a predetermined separation distance between the puller wire and a neutral bending axis of the beam. The layer and the tubing may be bounded to the beam by one or more heat shrinking tubing.

The present invention includes a method of manufacturing the aforementioned catheter, including wrapping the tubular structure of the deflectable section in one or more heat shrink tubing to form a tube assembly, heating the one or more heat shrink tubing to recover around the second tubular structure; and heating the tube assembly to reflow at least inner layers of the first and second tubular structures to form the interlocking nodes. The one or more heat shrinking tubings may be removed after the tubular structures have been sufficiently reflowed.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIG. 2C is an end cross-sectional view of the catheter body of FIG. 2, taken along line C-C.

FIG. 3 is a perspective view of the deflectable section of FIG. 1, shown partially broken away.

FIG. 3A is a top view of a joint bracket in accordance with one embodiment.

FIG. 4 is a perspective view of a joint bracket pair in accordance with another embodiment, as mounted on a deflection beam.

FIG. 4A is a perspective view of one bracket of FIG. 4.

FIG. 4B is a perspective view of another bracket of FIG. 4.

FIG. 12 is a top plan view of a tapered deflection beam without sloped sections, in accordance with one embodiment.

FIG. 12A is a top plan view of the deflection beam of FIG. 12 with brackets mounted thereon.

DETAILED DESCRIPTION OF THE INVENTION

Figure 1:
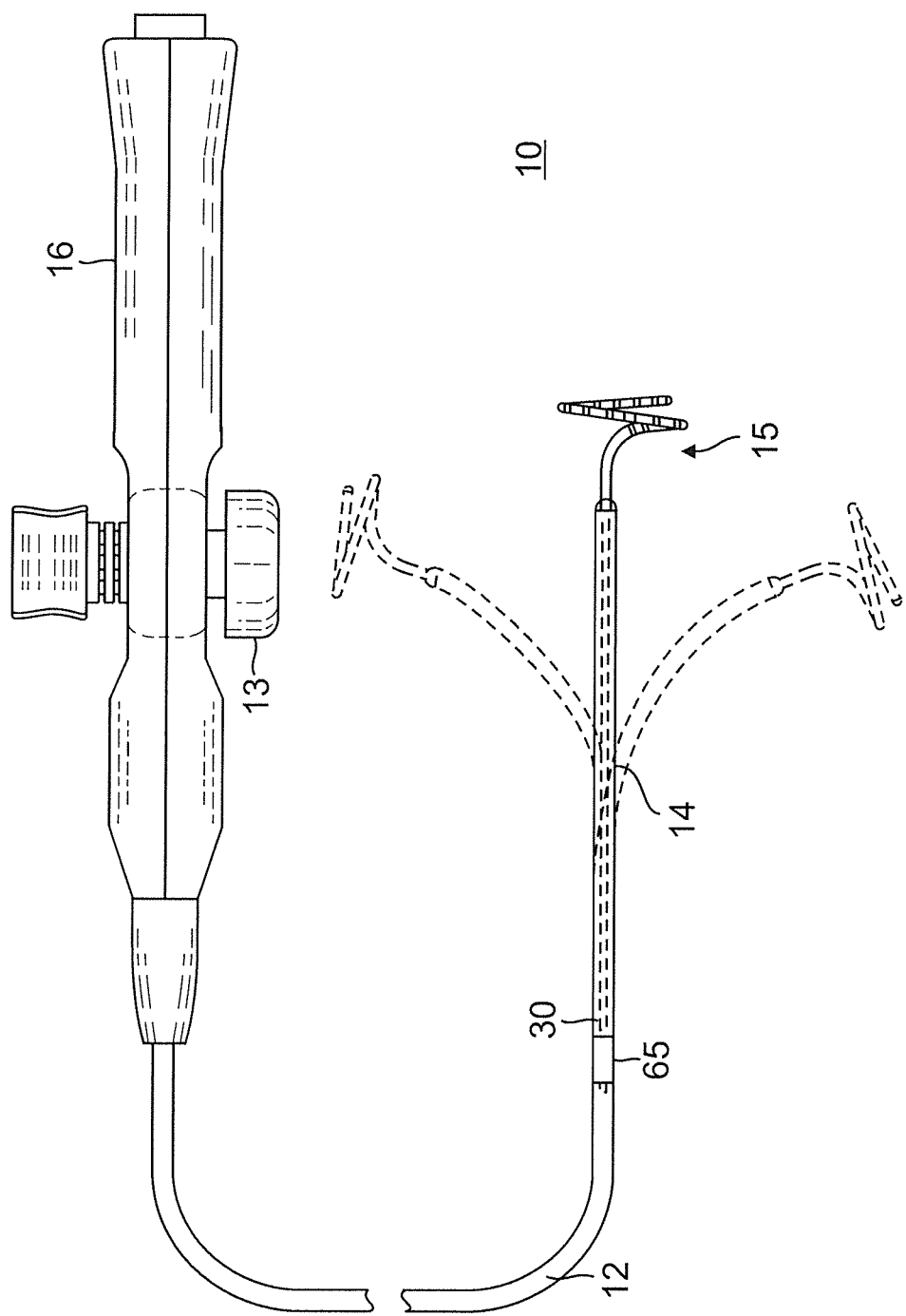
FIG. 1 is a top plan view of a catheter in accordance with one embodiment of the present invention.

The present invention is directed to a catheter having a catheter body (or shaft) and a deflectable distal portion having an elongated flat beam or "blade" to effectuate precise on-plane bi-directional deflection while maximizing space within the catheter for components including lead wires, puller wires, cables, tubings and any other support members for advanced distal tip designs. With reference to FIG. 1, a catheter 10 in accordance with an embodiment of the present invention includes a catheter body 12, a deflectable distal section 14 distal of the catheter body, and a control handle 16 proximal of the catheter shaft. The deflectable section 14 has a tip assembly 15 having, for example, a lasso design with a generally circular main portion extending and oriented transversely from a distal end of the deflectable section 14. Bi-directional deflection is effectuated by user manipulation of an actuator 13 provided on the control handle 16 which moves a puller wire that extends along the catheter from the control handle 16 through the catheter body 12, and into the deflectable section 14.

Figure 2:
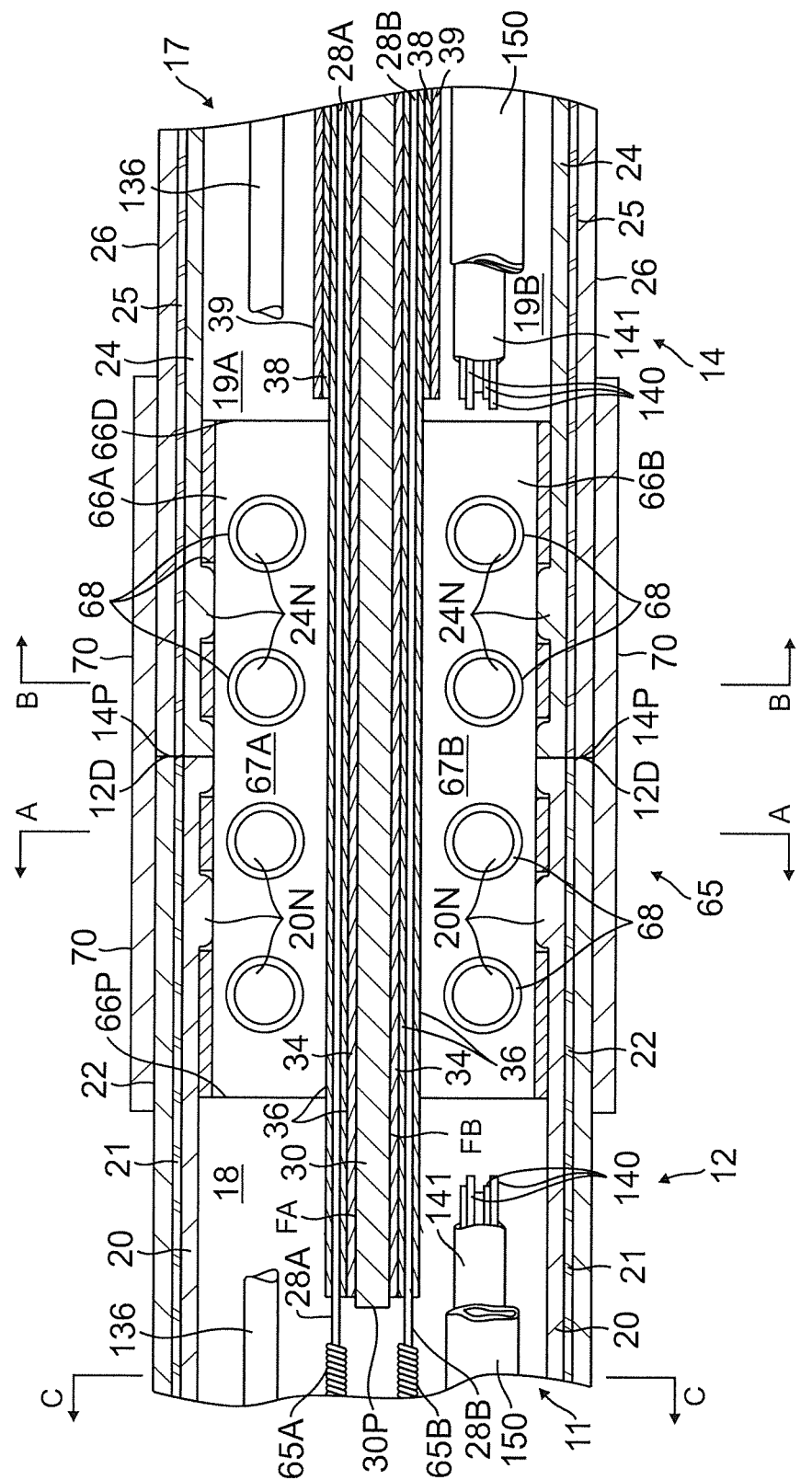
FIG. 2 is a side cross-sectional view of a transition section between a catheter body and a deflectable section of the catheter of FIG. 1 in accordance with one embodiment of the present invention.
Figure 2A:
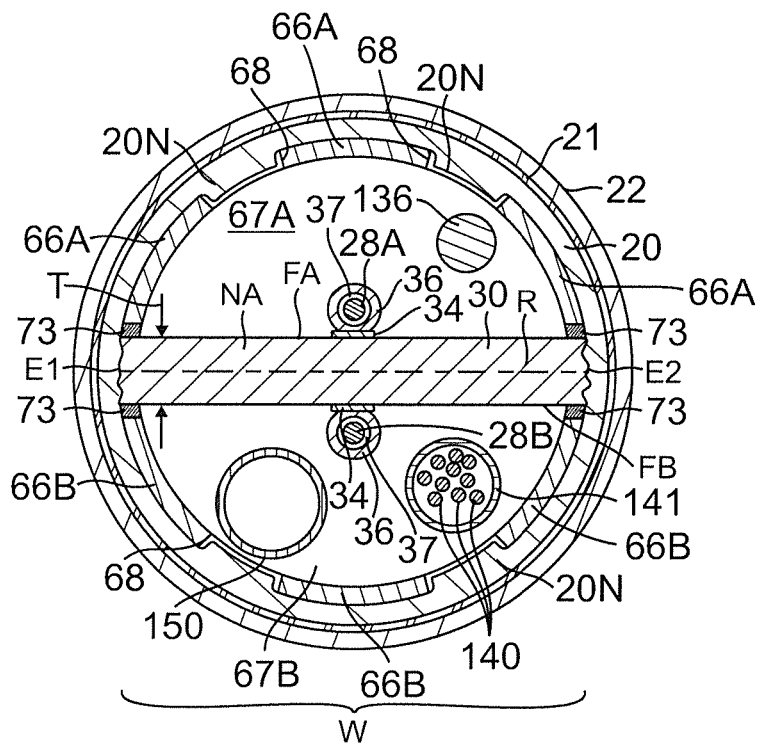
FIG. 2A is an end cross-sectional view of the transition section of FIG. 2, taken along line A-A.

With reference to FIGS. 2 and 2A, the catheter body 12 is an elongated tubular structure 11 comprising a single, central or axial lumen 18. The catheter body 12 is flexible, i.e., bendable, but substantially non-compressible along its length. The catheter body 12 may be of any suitable construction and made of any suitable materials. In one embodiment, the catheter body 12 is multi-layered comprising at least an inner coat or layer 20, and an outer coat or layer 22 with an imbedded braided mesh 21 of stainless steel or the like to increase torsional stiffness of the catheter body 12 so that, when the control handle 16 is rotated, the deflectable section 14 of the catheter 10 rotates in a corresponding manner. The outer diameter of the catheter body 12 is not critical, but is preferably no more than about 8 French. Likewise the thicknesses of the layers 20 and 22 are not critical.

Figure 2B:
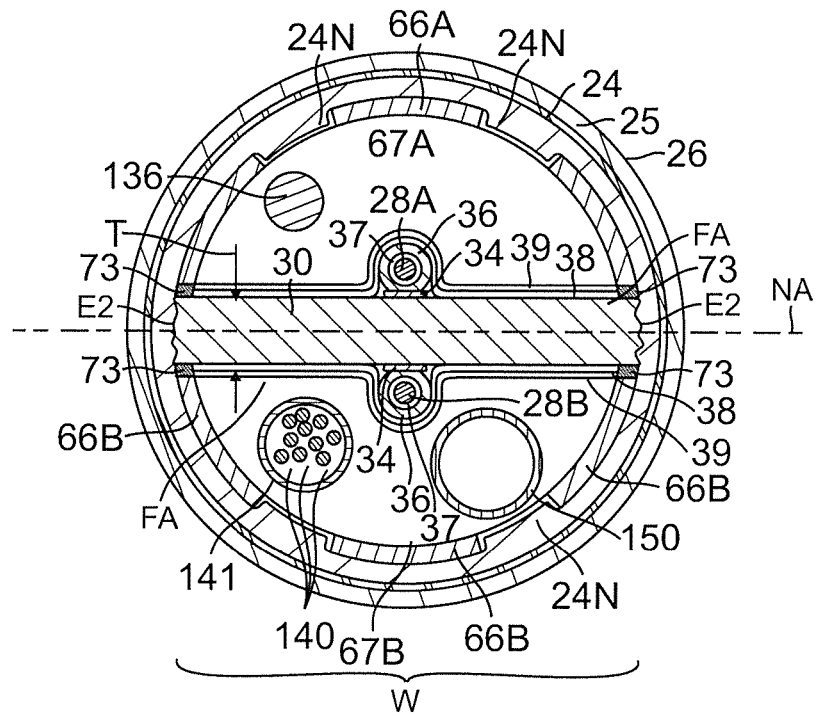
FIG. 2B is an end cross-sectional view of the transition section of FIG. 2, taken along line B-B.

The deflectable section 14 has a tubular structure 17 with construction similar to the tubular structure 11 of the catheter body 12 except with greater flexibility. In the embodiment of FIGS. 2 and 2B, the deflectable section 14 has a central lumen 19 and a multi-layered construction comprising at least an inner coat or layer 24, and an outer coat or layer 26 with an imbedded braided mesh 25 of stainless steel or the like. The outer diameter of the deflectable section 14 is similar to the catheter body 12, at preferably no more than about 8 French.

Suitable materials for the layers of the catheter body 12 and the deflectable section 14 include materials with moderate heat deflection temperatures so stiffness of the deflectable section 14 and thus its deflection characteristics are not modified by introduction into the patient's body due to temperature variations. Suitable materials for the inner and outer layers 20 and 22 of the catheter body 12 include Pebax and Pellethane. Materials particularly suitable for both the inner and outer layers 20 and 24 include lower shore hardness plastics ranging from about 25-55 D.

Suitable materials for the inner and outer layers 24 and 26 of deflectable section 14 include polyurethane or Pebax. In one embodiment, the tubular structure 17 of the deflectable section 14 includes an extruded braided structure, with the inner layer 24 having a thickness ranging between about 0.002 inch to 0.003 inch of natural "sticky" 2533-SA-01 PEBAX, then braided with 0.0016 inch diameter, PEN braid (50-80 pics per inch), and the outer layer 26 including extruded PEBAX 5533-SA-01 or 4033-SA-01 PEBAX with about 25% barium sulfate added for radiopacity.

Extending through the length of the deflectable section 14 is an elongated support structure configured as a flat beam or "blade" 30 with a rectangular cross-section R having a greater width W and a lesser thickness T, as shown in FIG. 2B, defining two opposing rectangular face surfaces FA and FB (or sides, used interchangeably herein) that are flat and smooth, and two outer longitudinal side edge surfaces E1 and E2 that are friction-inducing, e.g., uneven, rough, textured and/or serrated. The beam 30 may be constructed of any suitable high yield strength material that can be straightened or bent out of its original shape upon exertion of a force and is capable of substantially returning to its original shape upon removal of the force. Suitable materials for the beam include full hard, cold worked stainless steel alloys (304 or 316 full hard condition), nickel/titanium alloys (nitinol) or phosphor bronze alloys. Nitinol alloys typically comprise about 55% nickel and 45% titanium, but may comprise from about 54% to about 57% nickel with the balance being titanium. A suitable nickel/titanium alloy is nitinol, which has excellent shape memory, together with ductility, strength, corrosion resistance, electrical resistivity and temperature stability. The width W of the beam generally equals the inner diameter of the deflectable section 14. Accordingly, the beam 30 is situated inside the deflectable section 14 to effectively divide or bisect the central lumen 19 into two sub-lumens, e.g., equal half cylindrical spaces 19A and 19B, with components such as lead wires, cables, and tubings passing through either space.

The catheter 10 has exceptional torque transmission capability provided by a joint or transition section 65 between the catheter shaft 12 and the deflectable section 14, as shown in FIGS. 2, 2A and 2B. The transition section 65 transfers torsional forces from the control handle 16 to the distal assembly 15 with high fidelity and low hysteresis, to provide a user with a means to accurately place and control the distal assembly 15 within the patient. The transition section 65 includes a pair of opposing, elongated half-cylindrical members or brackets 66A, 66B, e.g., formed by die cutting or acid etching, with circular perforations or punched through-holes 68 arranged in a predetermined pattern. In one embodiment, there are 11 through-holes and the pattern includes a plurality of transverse rows, with adjacent rows offset by a predetermined distance, although it is understood that other alternating or offset patterns would be suitable, as well. In the illustrated embodiment of FIG. 3A, the pattern has rows R1, R3, R5 and R7 with two through-holes each, and rows R2, R4 and R6 with one through-hole each, where rows R2, R4 and R6 are offset from rows 1, 3, 5 and 7 by about the diameter of a perforation. The brackets 66A, 66B can be constructed of the same material as the beam 30 and may be pre-coated with an adhesive for higher bond strength during heat fusion.

In the illustrated embodiment, each bracket has a uniform semi-circular or "C" shape cross section along its length and is affixed at its outer side edges 69, e.g., by laser welding 73, to a respective side of the beam 30. Having a curved or semi-circular cross-section, the C brackets 66A, 66B provide structural support to abutting ends of the tubular structures 11 and 17 at the transition section 65. In the illustrated embodiment, the brackets 66A and 66B are affixed to the beam 30 near the proximal end 30P (which extends a short distance proximally past the joint 65 between the catheter body 12 and the deflectable section 14). So affixed, the members 66A and 66B along with the side edges E1 and E2 form a full cylindrical hollow body 66 (FIG. 3) with a circumferential contour substantially encircling the beam 30 at the transition section 65. As best shown in FIG. 2B, the full cylindrical body 66 (used interchangeably with the brackets 66A, 66B) defines a central lumen 67 that is bisected by the beam 30 into two semi-circular cavities 67A and 67B through which components, such as lead wires, cables, etc., can pass.

With reference to FIGS. 2 and 3, in assembling the catheter and the transition section 65, a distal end 11D of the tubular structure 11 of the catheter shaft 12 is slid onto proximal end 66P of the cylindrical body 66. A proximal end 17P of the tubular structure 17 deflectable section 14 is slid onto distal end 66D of the cylindrical body 66, with the beam 30 extending through the lumen 19 of the deflectable section 14. Accordingly, distal end of the tubular structure 17 and proximal end of the tubular structure 11 cover the body 66 from opposite directions such that they abut each other at or near a mid-location along the length of the body 66, which can range between about 5 mm and 12 mm, preferably about 6.5 mm and 10 mm.

The inner coatings 20 and 24 of the tubular structures 11 and 17, respectively, are then fused to the body 66, with application of sufficient heat and pressure so as to melt and flow into the perforations 68 forming nodes 20N and 24N. The fusion creates a very strong interlocking bond between the tubular structures of the catheter shaft 12 and the deflectable section 14. The nodes 20N and 24N increase the axial load capacity to the joint 65. In fact, the resulting torque transmission bond joint can be stronger in torsion and tensile force loading than the braided catheter body 12 and deflection section 14 that are bonded to it. The friction-inducing edges E1 and E2 of the beam 30 within and in contact with the body 66 also help grab the inner layers 20 and 24 and prevent slippage between the beam 30 and the tubular structures 11 and 17.

To facilitate the application of heat and pressure to the transition section 65, one or more protective heat-shrink tubing 70 (FIG. 2), e.g., fluorinated ethylene propylene (FEP) or polyethylene terephthalate (PET), is placed and shrunken (or "recovered") over the transition section (e.g., by a heat gun or oven). The transition section 65 covered by the heat-shrink tubing(s) 70 is then placed in a two-piece heat fusing die head (not shown) for heating to melt (or "reflow") the inner layers 20 and 24 into the perforations 68, followed by cooling. The shrink tubing 70 can be used as a process aid to prevent the melted layers from contacting the heated die and create a uniform transition between mating ends of the deflectable section 14 and the catheter body 12. Thus, the shrink tubing 70 is removed from the transition section 65 after the fusing process.

The heat fusing die head utilizes a highly accurate fusing die height measurement indicator (LVDT) to sense fusing die head movement during the heating/fusing process. Since the construction materials of the layers of the shaft 12 and the deflection section 14 may include extruded raw thermoplastic polymers with a wide range of heat histories (±25° F.) between material lots, monitoring the softening of the polymers and the resultant die head movement is another means besides temperature measurement to achieve process control while reducing the influence of polymer heat history during the heating/fusing process. Moreover, the transition section can be created in minimal duration (e.g., less than about 60 seconds) using a thermal fusing machine that is water-cooled to provide fast cycle times. The resulting transition section is advantageously homogenous and seamless. The structure is nondiversified once heat-pressure fuse operation is completed.

Figure 4C:
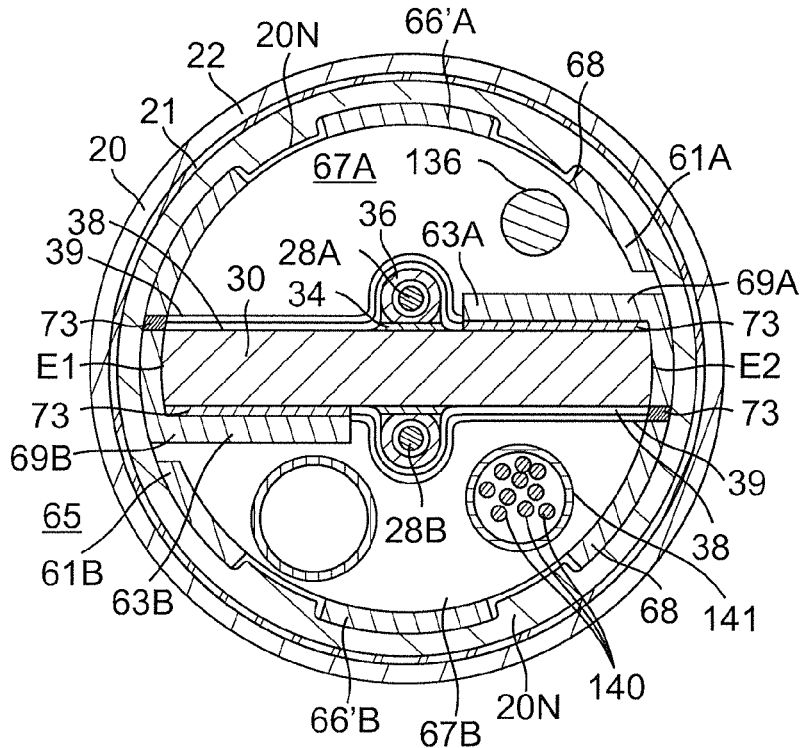
FIG. 4C is an end cross-sectional view of a transition section employing the joint bracket pair of FIG. 4.

In an alternate embodiment as shown in FIGS. 4-4C, each elongated half-cylindrical bracket 66'A, 66'B includes a planar portion 63A, 63B that is flat and rectangular. The planar portion is adjoined to the respective half-cylindrical bracket along a longitudinal side edge 69 at a nontangential angle θ (FIG. 4A) of about 90 degrees measured between the planar portion and a tangent T off side edge 69. Accordingly, each member 66'A, 66'B has a uniform cross-section along its length resembling a horizontal letter "G". The G brackets 66'A and 66'B with their respective planar portions 63A and 63B can be formed from a single rectangular piece of die cut sheet that is bent along the longitudinal side edge 69A or 69B. In the illustrated embodiment, the G brackets 66'A and 66'B are affixed to the beam 30 near its proximal end 30P (FIG. 4) with each member opposing each other from opposite sides FA and FB of the beam 30. Each portion 63A, 63B is affixed to a respective surface FA, FB, e.g., by weld 73, leaving free edge 61A and 61B unattached and free floating. In the illustrated embodiment, the width of each planar portion 63A, 63B is about half the diameter of a half-cylindrical bracket 66'A, 66'B.

Opposing and upside down from each other, the G brackets 66'A and 66'B jointly form nearly a full cylindrical body 66' (with the exception of the unattached edge 61A and 61B) substantially encircling the beam 30 at the transition section 65, with the planar portions 63A, 63B extending diametrically toward each other sandwiching the beam 30 therebetween. The portions 63A, 63B are thus parallel to each other, and parallel and coplanar with the beam. The body 66' (used interchangeably with the half-cylindrical brackets 66'A, 66'B) defines a central lumen that is bisected by the beam 30 (and the portions 63A, 63B) into two semi-circular cavities 67'A and 67'B through which components, such as lead wires, cables, etc., can pass. So joined, the members 66A', 66'B and the beam 30 have a cross-section resembling the letter "S". Because only the planar portions 63A, 63B are affixed to the beam leaving edges 61A, 61B free floating, each half-cylindrical bracket 66'A, 66'B acts as a "spring" to provide an outward force when pressed on by the inner layers 20 and 24 during heat recovery of the heat shrinking tubing 70 and the reflowing of the inner layers 20 and 24. The outward force ensures larger and deeper nodes 20N and 24N and therefore a better bond between the G brackets 66'A and 66'B and the tubular structures 11 and 17 of the catheter body 12 and deflectable section 14. The planar portions 63A and 63B provide large flat surface areas for clamping the G brackets 66'A and 66'B and the beam 30 together to provide a better setup in preparation for resistance or laser welding these components together in terms of minimizing the gap between the welded surfaces and enabling axial alignment between the beam and the brackets. The large flat surfaces also ensure better contact between contact surfaces of the planar portions 63A and 63B and the beam 30 for a better and stronger weld.

Figure 5A:
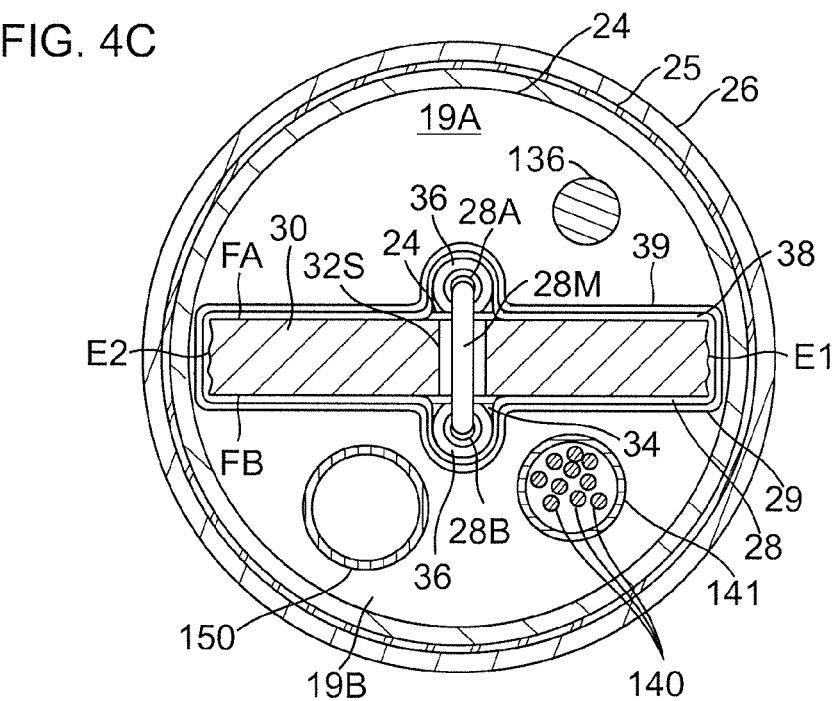
FIG. 5A is an end-cross sectional view of the deflectable section of FIG. 5, taken along line A-A.
Figure 5:
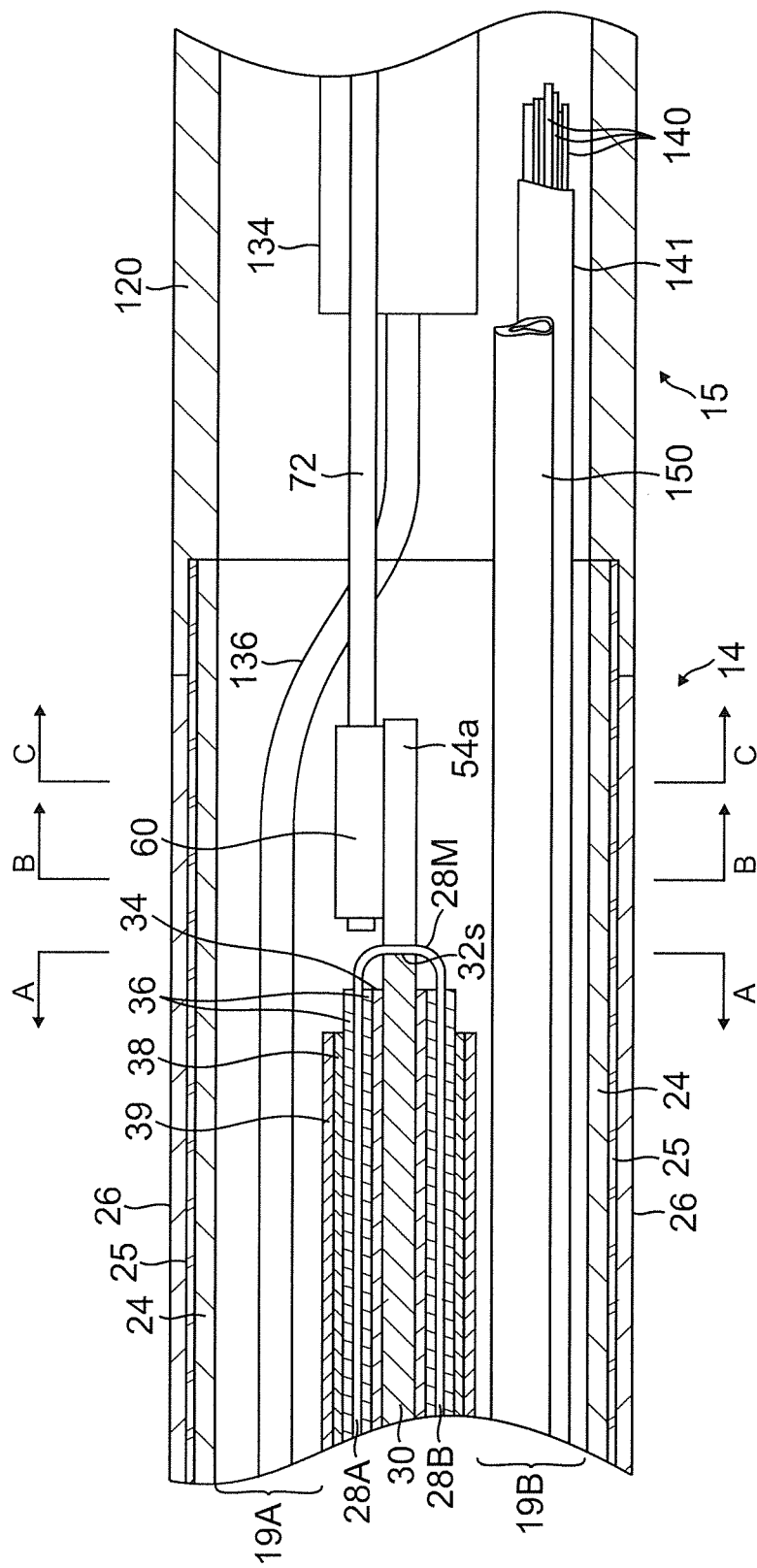
FIG. 5 is a side cross-sectional view of a junction between the deflectable section and a distal assembly of the catheter of FIG. 1, in accordance with an embodiment.
Figure 5B:
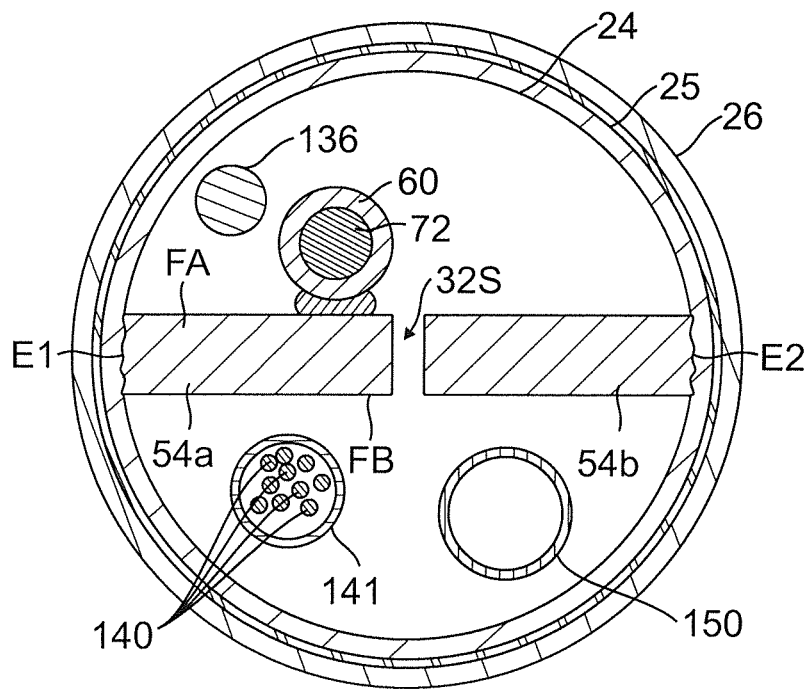
FIG. 5B is an end-cross sectional view of the deflectable section of FIG. 5, taken along line B-B.
Figure 5C:
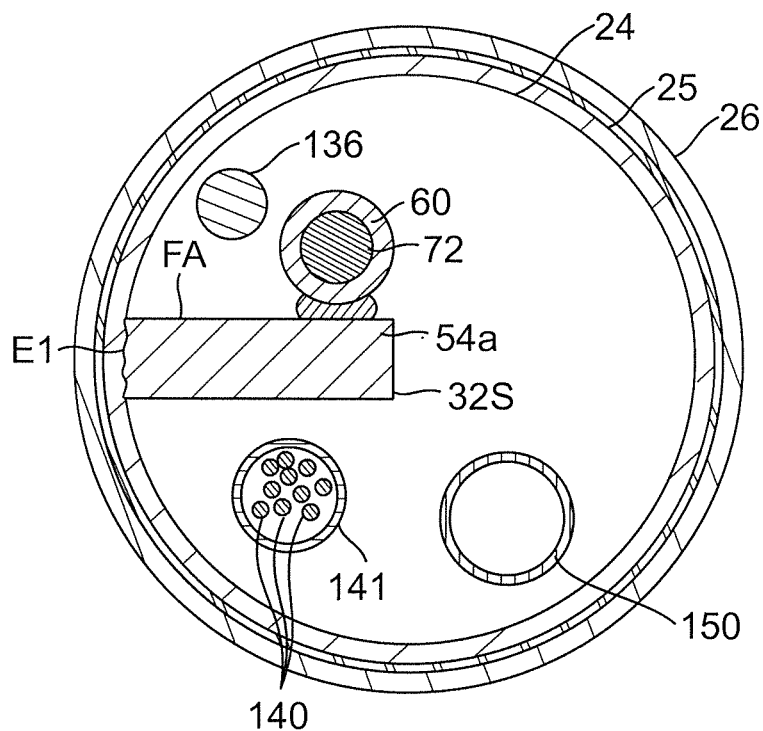
FIG. 5C is an end-cross sectional view of the deflectable section of FIG. 5, taken along line C-C.
Figure 6A:
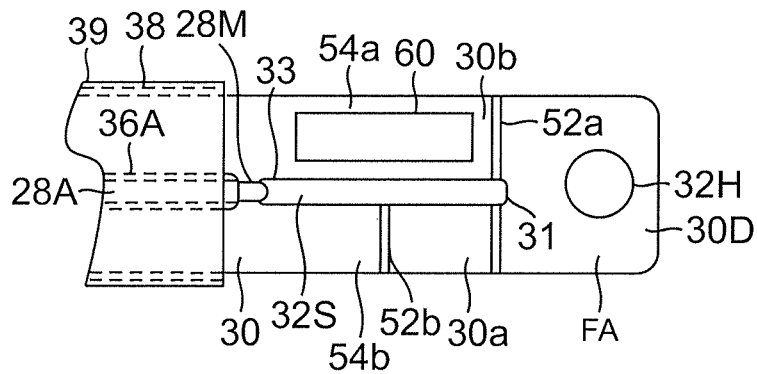
FIG. 6A is a top plan view of a distal end of the deflection beam according to one embodiment.
Figure 6B:
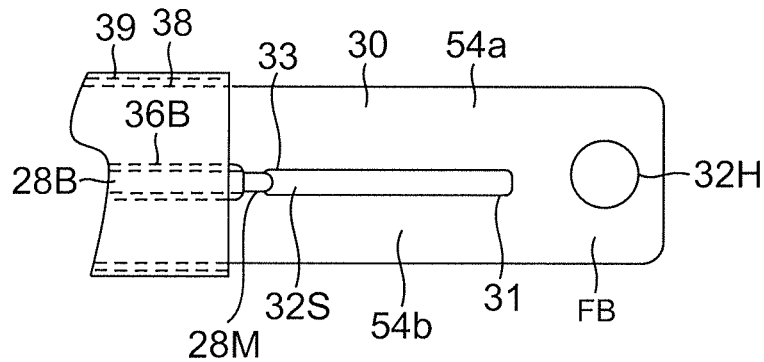
FIG. 6B is a top plan view of a distal end of the deflection beam of FIG. 6A, in an original configuration.
Figure 6C:
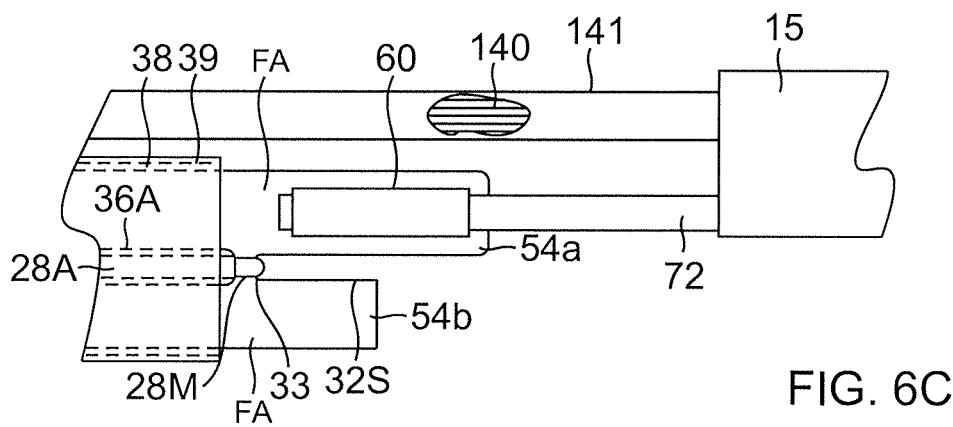
FIG. 6C is a top plan view of a distal end of the deflection beam of FIG. 6A, as attached to components of the distal assembly, according to one embodiment.

An accordance with a feature of the present invention, the catheter 10 provides bi-directional deflection with a single continuous puller wire 28 that advantageously requires less actuation force by a user and imposes less shear stress on the puller wire. The puller wire 28 has a U-bend mid-portion 28M being a distal-most portion of the puller wire in the catheter. As shown in FIG. 5, the U-bend mid-portion 28M divides the puller wire into two longitudinal portions 28A and 28B of generally equal length, each with a proximal end that is anchored in the control handle 16. With reference to FIGS. 6A, 6B and 6C, to anchor the U-bend portion 28M at a distal location on the catheter, a distal end of the beam 30 has a receiving formation 32 e.g., either an on-axis slit 32S or an on-axis through-hole 32H, which securely receives the mid-portion 28M so that each long portion 28A and 28B extends longitudinally centered on the beam along a respective face surface FA, FB of the beam 30. This arrangement advantageously avoids the use of conventional T-bars, crimp type connections, soldering or welding as a means to anchor a distal end of the puller wire to the beam 30. And, because the puller wire is not rigidly attached to the beam 30, this arrangement provides smooth bi-directional steering.

As illustrated in FIGS. 6A and 6B, the distal end 30D of the beam 30 has an original configuration prior to assembly of the catheter and attachment of the puller wire 28, which includes an elongated longitudinal closed slit 32S with a distal end 31 and a proximal end 33. The slit 32S is disposed immediately proximal of a distal end portion 30D of the beam 30. The through-hole 32H is disposed in the distal end portion 30D. The U-bend mid portion 28M of the puller wire may be inserted and hooked through the hole 32H, or alternatively in the slit 32S at its proximal end 33. In the latter regard, the slit 32S is adapted into an open configuration (FIG. 6C) from a closed configuration (FIG. 6A) for receiving the U-bend mid-portion 28M when the distal end portion 30D of the beam is detached by a user bending or cutting along a transverse "pre-cut" groove 52 (FIG. 6A) provided on the face FA of the beam 30 proximal of the hole 32H. In the illustrated embodiment, a first transverse groove 52a is aligned with the distal end 31 of the slit 32 and a second (half width) transverse groove 52b is aligned at or near a midpoint along the length of the slit 32S. Thus, the distal end portion 30D can be readily broken off or otherwise detached from the beam along the groove 52a. For easier access to the open slit 32S, portion 30a can be detached from the beam 30 along the groove 52b, as shown in FIG. 6C. The puller wire portions 28A and 28B extend proximally along opposites sides FA and FB of the beam 30 through the deflectable section 14, the central lumen 18 of the catheter body, and into the control handle 16.

As shown in FIG. 6C, the slit 32S is generally longitudinally centered and on-axis with the longitudinal axis of the beam 30 such that the slit divides the beam into two generally equal elongated sections or prongs 54a, 54b. In the illustrated embodiment, a hollow tube or ferrule 60 (e.g., of stainless steel) is affixed e.g., by laser welding, to face FA of the prong 54b (although it is understood that the tube 60 may be alternatively affixed to prong 54a, with the portion 30b detached from the beam). A proximal end of a support member 72 supporting the distal assembly 15 is inserted and anchored in the tube 60, e.g., by crimping, to create an interference fit between the tube 60 and the support member 72 to transmit torque and tension/compression forces from the beam 30 to the distal assembly 15. A mechanical crimp process eliminates problematic adhesive bonding that can loosen or fail causing the distal assembly 15 to spin. A servo process with precision force control is used to detect a defined force slope so that acceptable interference between the support member 72 and the tube 60 is created without damaging the puller wire 28.

Proximal ends of the portions 28A and 28B are anchored in the control handle 16 and deflection mechanism in the control handle 16 responsive to the actuator 13 manipulated by a user is configured to draw or otherwise act on a proximal end of puller wire portion 28A or 28 to deflect the distal section 14 with a distinct curvature on side FA or FB of the beam 30. Throughout the catheter body 12, each puller wire portion extends through a respective compression coil 62A and 65B (FIGS. 2, 2C and 8) which is flexible but resists compression so that deflection of the catheter initiates at or near distal ends of the compression coils. Along the beam 30 in the deflectable section 14, each puller wire portion may be coated with PTFE or Teflon so the puller wires can slide smoothly inside a respective protective spacer tube 36 provided on a respective side of the beam 30 as discussed in further detail below.

As understood by one of ordinary skill in the art, the puller wire 28 is in tension to create a bending moment to deflect the beam 30 in the desired direction. Conventional catheter with a flat beam may use a puller wire with a rectangular cross-section that is welded and tightly constrained to the beam to prevent adhesion failure. While this design may be simple and compact in certain respects, the puller wire is under significant force due because of its close proximity to the beam, which in pure bending requires a substantial bending moment stress during deflection. In contrast, as illustrated in the drawings, including FIG. 2B, the catheter of the present invention is configured to provide a spacer of a predetermined thickness to separate the puller wire 28 and a neutral bending axis NA of the beam 30 by a predetermined distance so as to lower the force on the puller wire, including the bending moment. Moreover, the catheter 10 includes a puller wire 28 with a circular (or at least round) cross section to reduce the area moment of inertia, as an otherwise rectangular puller wire with the same cross-sectional area separated from the neutral axis by a comparable spacer would unduly increase the size/diameter of the catheter and the area moment of inertia to result in an unacceptably stiff catheter.

As shown in FIG. 2B, the spacer on each side of the beam 30 may include a spacer adhesive layer 34 and a wall of a lumened elastomeric puller wire spacer tube 36. The adhesive layer 34 may be provided by an ultra high temperature adhesive transfer tape sold by 3M under the model 100HT. The adhesive layer may have a thickness of about 0.001 inch and require about 72 hours to achieve full adhesive bond strength. The spacer tube 36, which may be constructed of polyimide, thin wall polyetheretherketone (PEEK), nylon or other thin wall thermoplastic tubing, is affixed to the adhesive layer 34, and a respective puller wire proximal portion 28A or 28B extends through lumen 37. An interior surface of the lumen 37 surrounding the puller wire may be coated with polytetrafluoroethylene (PTFE), e.g. TEFLON or TEFLON composite, to reduce static and dynamic friction with the puller wire. On each side FA and FB of the beam 30, the spacer runs longitudinally generally between the receiving formation 32S or 32H (FIG. 6A) and a proximal end 30P of the beam 30 (FIG. 2). Alternatively, the spacer may include an extrusion surrounding each puller wire portion. The extrusion may be made of PEEK.

The round puller wire 28 has a diameter D ranging between about 0.007 inch and 0.009 inch, and preferably about 0.008 inch. The beam 30 has a thickness T of about 0.004 inch and 0.007 inch, and preferably between about 0.005 inch and 0.006 inch. The puller wire and the neutral axis are separated by a distance d, ranging between about 0.008 inch and 0.025 inch, and preferably between about 0.010 inch and 0.015 inch. In one embodiment, the puller wire diameter D is 0.008 inch and a Nitinol 304V wire, and the beam thickness is 0.005 inch.

To constrain and secure the puller wire 28 on the beam 30 and as an additional means to prevent adhesive failure and detachment, at least a first inner heat shrink tubing 38 is placed on the beam 30, covering and surrounding the spacers on both sides FA and FB of the beam 30, inclusive of the puller wire portions 28A, 28B trained through the spacers (hereinafter referred to as "the beam assembly"). In the illustrated embodiments, including FIGS. 2B and 6A, the first inner heat shrink tubing 38 is followed by a second outer heat shrink tubing 39 that is placed over the beam assembly to surround and seal the components and the first heat shrink tubing 38. The first heat shrink tubing 38 may constructed of high temperature resistant polyester (PET) or fluorinated ethylene propylene (FEP) and have a wall thickness ranging between about 0.0005 inch and 0.004 inch, and preferably between about 0.00015 inch and 0.001 inch, in an expanded state. Another suitable material is polyester in terms of thin wall and high strength. The first heat shrink tubing 38 is recovered by heating with a hot air-based heating system thus providing a second bonding structure for the spacer tubes 36, as well as a first sealing structure for the adhesive layers 34 and spacer tubes 36. The uneven longitudinal edges E1 and E2 of the beam 30 help grab and secure the first heat shrink tubing 38 so it do not migrate or slip during deflection.

The second heat shrink tubing 39 may be constructed of extruded natural PEBAX, e.g., 2533-SA-01 (22 D shore hardness), thin wall with a thickness ranging between about 0.002 inch and 0.003 inch, or natural PELLETHANE (e.g., 80A shore hardness). The second heat shrink tubing 39 may be a layer of "sticky" low shore hardness thermoplastic elastomer which is heated and recovered over the first heat shrink tubing 38, thus creating a second layer sealing structure and a "sticky" heat bondable outer layer surrounding the beam assembly. The sticky outer layer provided by the second heat shrink tubing 39 is well suited to bond with the tubular structure 17 of the deflectable section 14 through a resistive heating process with clamp members to heat the beam 30.

The heat shrink tubings 38 and 39 extend from the distal end 30D of the beam to near the distal end of the brackets 66A, 66B, so as not to interfere with the weld 73 between the 66A and 66B and the beam 30. Depending on the length of the beam proximal of the brackets 66A, 66B, heat shrink tubings may be provided there as well.

Figure 7:
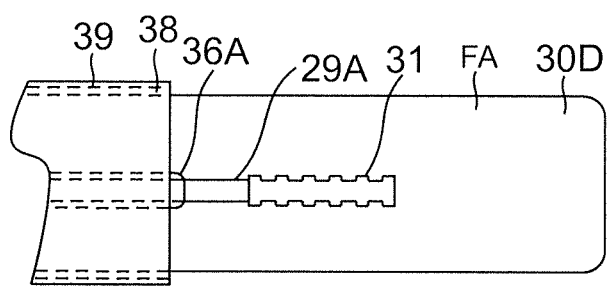
FIG. 7 is a top plan view of a distal end of the deflection beam according to another embodiment.

In another embodiment as illustrated in FIG. 7, a pair of tensile fibers 29, e.g., VECTRAN cords are utilized instead of puller wires. A crimped metal tube 31, e.g., of stainless steel or other alloys) is attached to the distal end of each fiber 29. Each tube 31 is affixed, e.g., by resistance- or laser-welded, to the longitudinal center of a respective side of the distal portion 30D of the beam. A respective spacer tube 36 surrounds each fiber and is bonded to a respective surface FA or FB of the beam by a spacer adhesive layer 34. The fibers 29 may be coated with low density polyethylene or TEFLON, e.g., DUPONT TRASYS 9825 or TRASYS 426 and MCLUBE 1829 TEFLON based coatings, to damp out noise and prevent stick-slip type non-uniform motion created by variations in dynamic and static friction coefficients during deflection. Food grade damping gel (e.g., Nye Lubricants fluorocarbon Gel 835C-FG//874//880FG) having synthetic hydrocarbon and PTFE or silicone and PTFE to coat the fibers 29 and interior of the spacer tubes 36.

Where the deflectable section 14 has a length greater than about 90 mm, one or more elongated flat beam stiffeners 80 may be mounted to either or both sides FA and FB of the beam 30 to modify and obtain desired curve geometry when the puller wire or tensile fibers (collectively referred to as "puller members") are activated via the control handle 16.

Figure 8A:
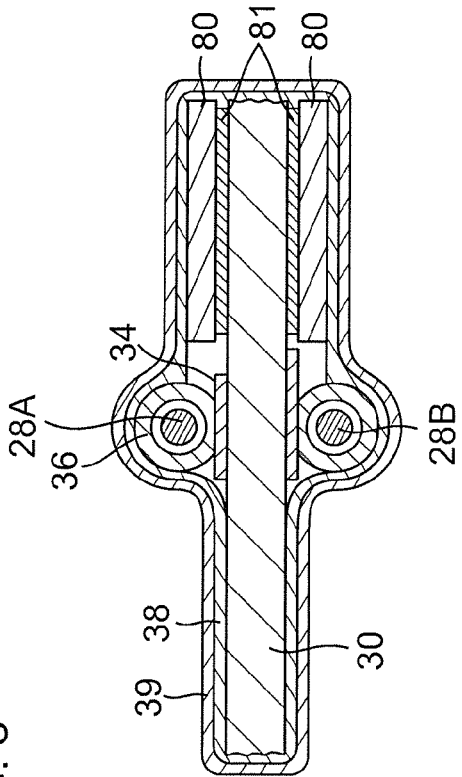
FIG. 8A is an end cross-sectional view of a deflection beam with beam stiffeners.
Figure 8:
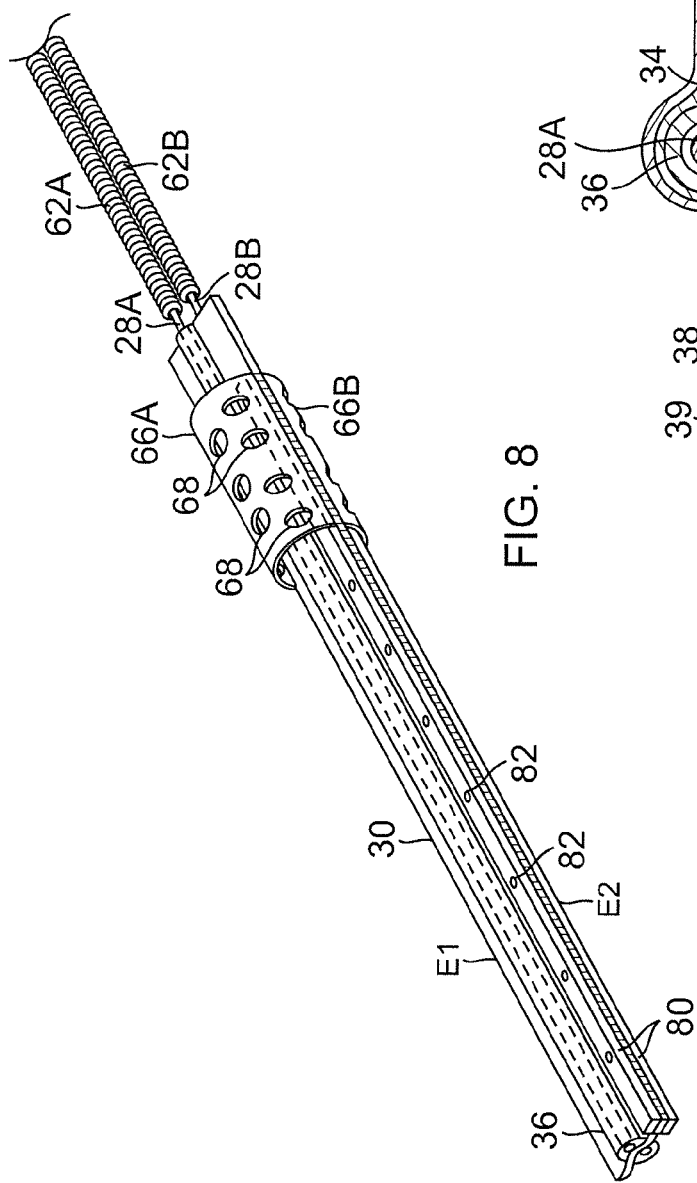
FIG. 8 is a perspective view of a deflection beam with beam stiffeners in accordance with one embodiment.
Figure 8B:
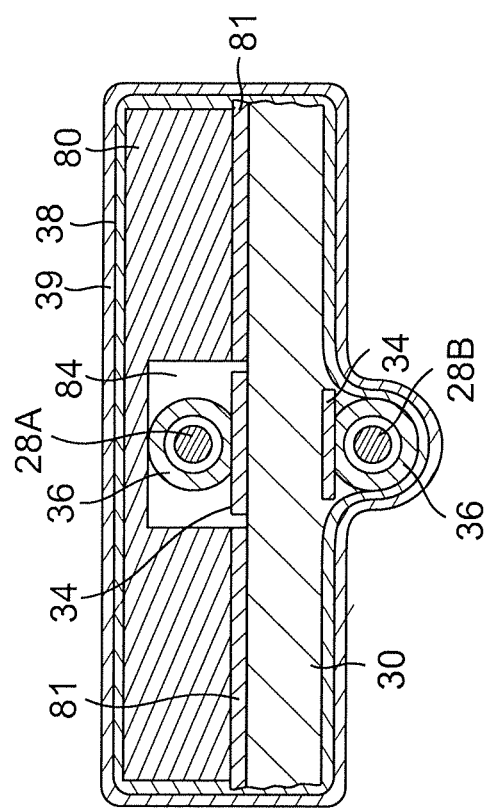
FIG. 8B is an end cross-sectional view of a deflection beam with a beam stiffener with a channel.

As shown in FIGS. 8, 8A, 8B, 8C, one or more stiffeners 80 may be adhesively bonded to the beam 30. The stiffeners 80 are generally parallel with the beam 30 and can have similar or different lengths relative to each other and the beam. The stiffeners may be bonded by a layer of adhesive 81 (FIGS. 8A and 8B), e.g., applied via ultra high temperature adhesive transfer tape sold by 3M under the name 110HT. The adhesive may have a layer thickness of about 1.0 mm. The adhesive provides a viscoelastic bond between the stiffeners and the beam. Alternatively, the stiffeners 80 may be spot welded by laser to the beam at selected locations 82 as shown in FIG. 8. It is understood that these two different bonding methods provide different degrees of stiffness despite employing beams and stiffeners of the same thicknesses due to the viscoelastic behavior of the adhesive bond compared to the metal-to-metal fusing of the spot welding bonds.

Figure 8C:
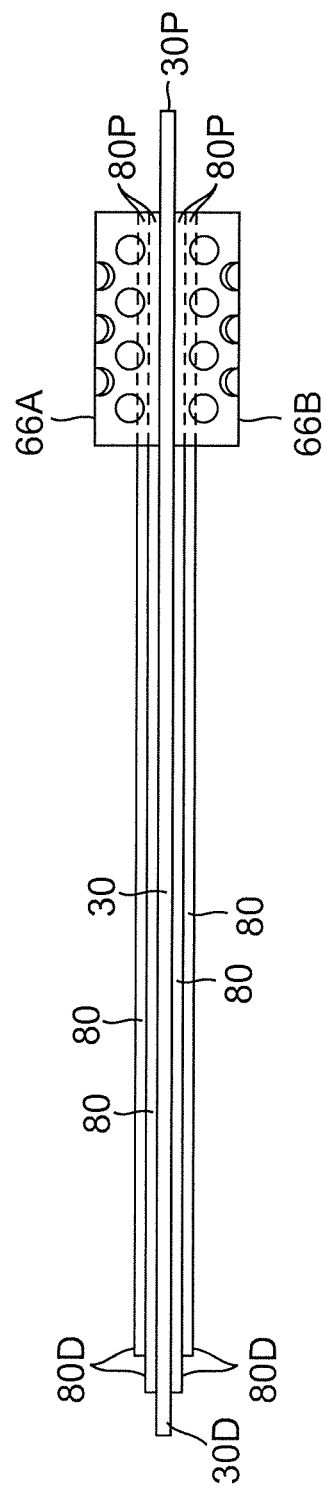
FIG. 8C is a side elevational view of a deflection beam with beam stiffeners affixed to the beam at their proximal ends.

In yet another alternate embodiment of FIG. 8C, proximal ends 80P of the stiffener beams 80 may be bonded to and rigidly supported by the beam 30 at or near the brackets 66 of the transition section 65, leaving distal ends 80D of the stiffener beams free floating and unattached, to create another type of curve. Moreover, depending on the shape and size of the stiffeners 80, a longitudinal channel 84 (FIG. 8B) to accommodate the puller wire and the spacer.

Figure 9:
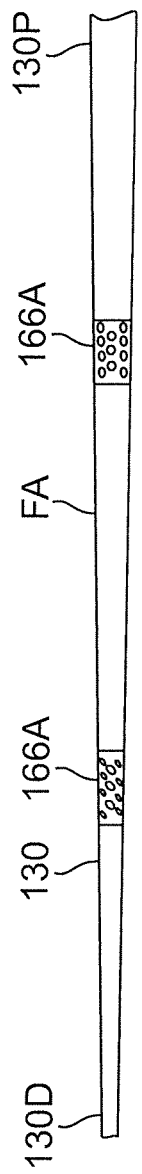
FIG. 9 is a top plan view of a tapered deflection beam, in accordance with one embodiment.
Figure 11:
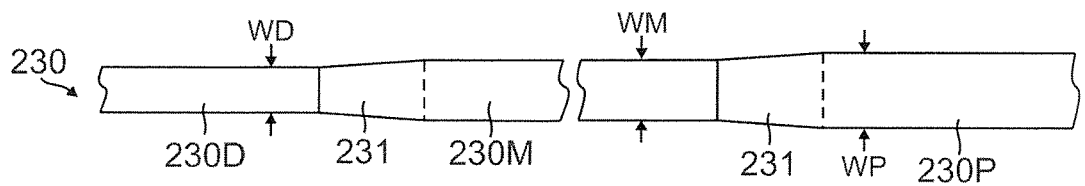
FIG. 11 is a top plan view of a tapered deflection beam with sloped sections, in accordance with one embodiment.

The cross section of the beam itself may change along its length. As illustrated in FIGS. 9, 11 and 12, each of beams 130, 230, 330 have a tapered configuration with the width W decreasing (continuously or discontinuously) from their proximal ends 130P, 230P, 330P to their distal ends 130D, 230D, 330D. The narrower distal end facilitates cannulation and tracking through smaller tubular regions, such as the great cardiac vein, and the larger proximal end provides more stability near larger tubular regions, such as the coronary sinus ostium when tracked inside the coronary sinus. The width of the beam may be gradually tapered, for example, in a linear manner, for a generally smooth profile along its side edges E1 and E2 (FIG. 9), or it may step-tapered in a manner along its length, with linearly sloped portions (FIG. 11) or without sloped portions (FIG. 12). It is understood that the beam may be constructed from multiple beam segments fused together end to end or as a single continuous elongated body. In one embodiment, the distal section 14 supported by the beam may have a proximal section with a 7 french diameter, a mid-section with a 6 french diameter and a distal section with a 5 french diameter.

In the embodiment of FIG. 9, where the beam 130 has the gradually tapered width, one or more pairs of brackets 166A and 166B are affixed to the beam 130 at selected locations forming generally a generally full cylindrical body encircling the selected locations. The selected locations for affixation of brackets (C or G brackets) may be a joint between beam segments and/or a joint where the width of the beam changes. The diameters of the brackets along their lengths vary correspondingly with the changing widths of the beam at those selected locations.

Figure 10:
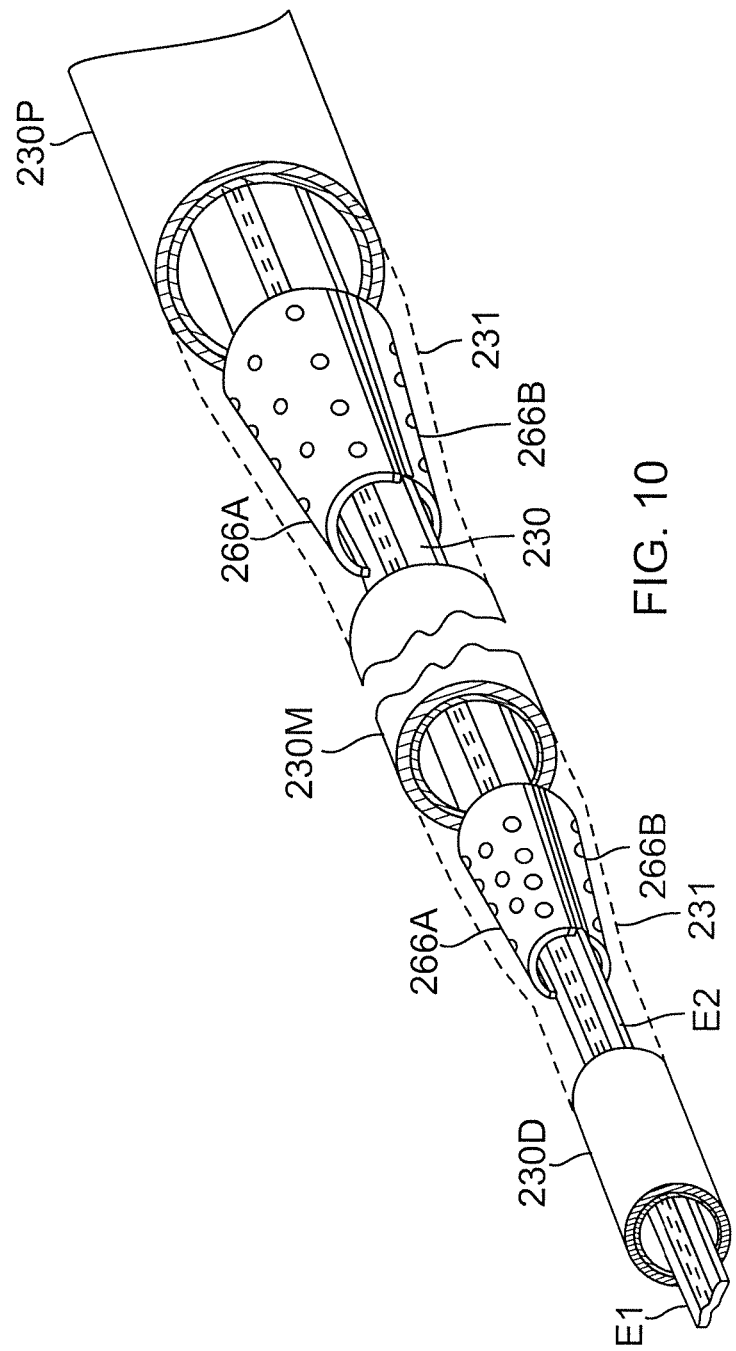
FIG. 10 is a perspective view of deflectable section with a tapered deflection beam with parts broken away, in accordance with one embodiment.
Figure 11A:
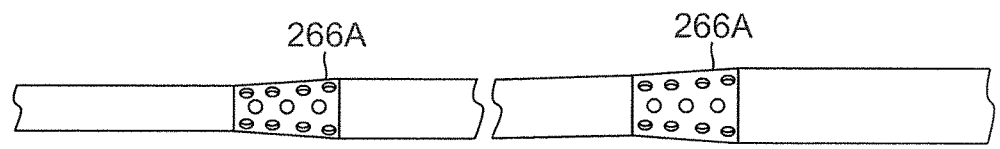
FIG. 11A is a top plan view of the deflection beam of FIG. 11 with tapered brackets mounted thereon.
Figure 11B:
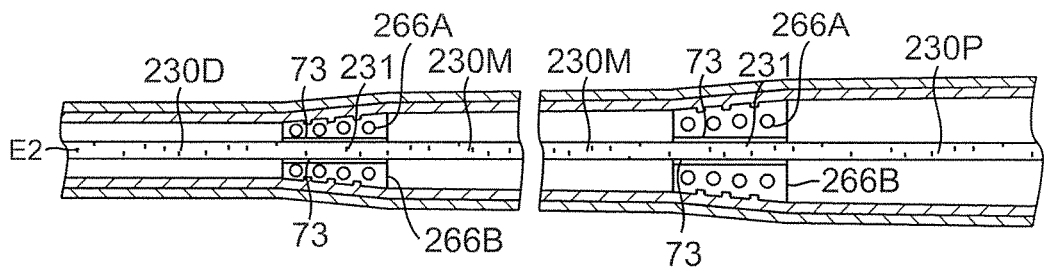
FIG. 11B is a side elevational view of the deflection beam and brackets of FIG. 11A with a reflowed tubular structure shown partially broken away, according to one embodiment.
Figure 11C:
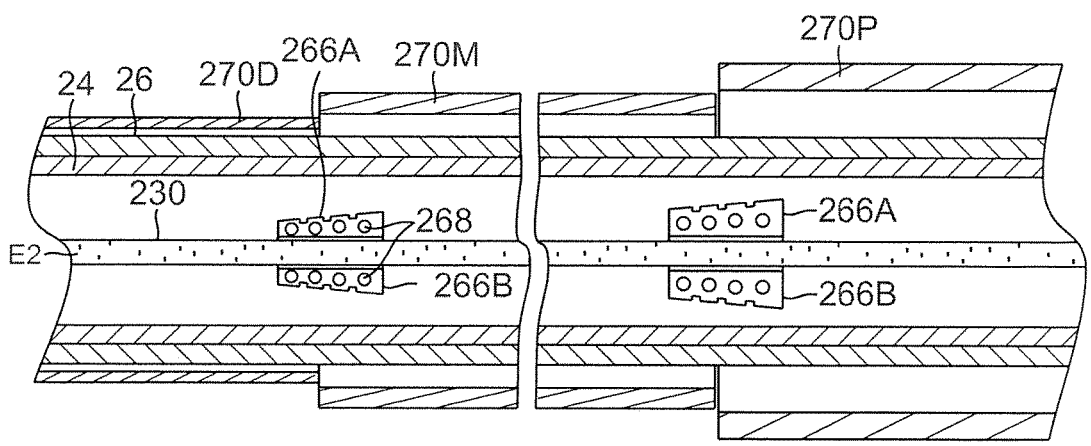
FIG. 11C is a side elevational view of the deflection beam, brackets and tubular structure of FIG. 11B, with heat shrinking tubings prior to recovery and reflowing.

In the embodiment of FIGS. 10 and 11, the beam 230 has a step-tapered configuration with rectangular sections 230D, 230M, 230P adjoined by sloped sections 231 therebetween. Each rectangular section has a respective width which is uniform throughout that section. However, the more distal rectangular sections have smaller widths than the more proximal rectangular sections such that WD<WM<WP where WD is the width of the most distal section 230D, WM is the width of the mid section 230M and WP is the width of the most proximal section 230P. Between each rectangular section is a sloped section 231 whose width changes linearly (by decreasing in the distal direction or increasing in the proximal direction) along its length so that the sloped section 231 bridges the adjacent rectangular sections 230 without sharp bends or corners on side edges E1 and E2 of the beam. The slope of each section as measured relative to the longitudinal axis of the beam ranges between 0 and less than 90 degrees, preferably between about 15 and 30 degrees. In the illustrated embodiment, the beam 230 includes three rectangular sections 230 and two sloped sections 231 in between and alternating with the rectangular sections 230. As shown in FIGS. 11A and 11B, a pair of brackets 266A and 266B (266B not shown) are mounted on each tapered section 231 forming generally a full cylindrical body encircling each tapered section. Each pair of bracket conform with their respective tapered section 231 with a diameter that also changes along its length so as to be similarly tapered as the respective section 231.

Alternatively, in the embodiment of FIGS. 12 and 12A, the beam 330 has a nonlinear or step-tapered configuration having rectangular sections 330 directly adjoined to each other without sloped sections. Thus, the side edges E1 and E2 have a "step" profile with corners 331. Rectangular sections 330D, 330M and 330P have uniform widths WD, WM or WP, respectively, wherein WD<WM<WP. A pair of brackets 366A and 366B (366B not shown) are mounted at or near each corner 331 forming a generally full cylindrical body overlapping the distal end and proximal end of adjacent pairs of rectangular sections 230. The diameter of each bracket may be uniform along its length and conform with the narrower width of the adjacent pairs of rectangular sections 231.

A method of assembling a tapered beam, for example, the beam 230 is described below in reference to FIG. 10, although it is understood that the method may be used for any beam, including the beam 130 or the beam 330. A continuous section of tubing 217 (comprising, e.g., extruded inner layer 24 and outer layer 26 with an embedded braided mesh 25, as described above) is placed over the beam, as illustrated in FIG. 11B. The tubing 217 has a sufficient length to cover the beam longitudinally and a suitable diameter that is large enough to accommodate all widths of the beam. Where the beam has a plurality N of cylindrical bodies 266, a plurality of at least (N+1) heat shrink tubings 270 are placed over the tubing 217 with ends of adjacent tubes 270 abutting at or near a midpoint of each cylindrical body 266. The heat-shrink tubings 270 may be fluorinated ethylene propylene (FEP) or polyethylene terephthalate (PET). Each heat shrink tube 270 may have a distinct diameter that corresponds with the width(s) of the section(s) 230 or 231 it covers. In the illustrated embodiment of FIG. 10, there are three heat shrink tubings 270D, 270M and 270P, with respective diameters DD, DM and DP wherein DD<DM<DP.

The heat shrink tubings 270 are recovered by application of heat (e.g., by a heat gun) and then placed in a two-piece heat fusing die head (not shown) for heating to reflow the tubing 217 of the deflectable section 14, which conforms the tubing 217 to the cylindrical brackets 266A and 266B and fuses the inner layer 24 to the brackets by means of melted material flowing into perforations 268 to form nodes interlocking the tubing 217 and the brackets 266A and 266B. Textured side edges E1 and E2 of the beam 230 also help minimize slippage between the beam 230 and the tubing 217. Thereafter, the heat shrink tubings 270 can be removed from the tubing 217.

Alternatively, the tubular structure 17 of the deflectable section 14 may be constructed by injection molding, instead of extrusion and reflow.

In the illustrated embodiment of FIG. 1, the distal assembly 15 comprises a generally straight proximal region and a generally circular main region having at least one loop circling about 360 degrees, if not two loops circling about 720 degrees. The proximal region is mounted on the deflectable section 14 and the main region carries a plurality of electrodes (ring and/or tip) for mapping and/or ablation. With reference to FIG. 5, the distal assembly 15 includes the shape memory support member 72, lead wires 140 for the electrodes carried on the distal assembly 15, and a cover 120 extending the length of the distal assembly. The lead wires 140 attached to the electrodes on the distal assembly 15 extend through a nonconductive sheath 141 which extends from the distal assembly through the lumen half 19B of the deflectable section 14, through the cavity half 67B of the transition section 65, through the lumen 18 of the catheter shaft 12, and into the control handle 16. Ring electrodes may also be carried on the deflectable section 14, as shown in FIG. 3.

An electromagnetic position sensor 134 (FIG. 5) is mounted in or near the distal end of the deflectable section 14 or the proximal end of the distal assembly 15. A sensor cable 136 extends from the sensor 134 into the half lumen 19A of the deflectable section 14, the cavity half 67B of the transition section 65, the central lumen 18 of the catheter body 12 and into the control handle 16 where it terminates in a suitable connector (not shown).

The catheter 10 may also be adapted for irrigation at the distal assembly 15, for example, to supply fluid at or near the electrodes of the distal assembly. To that end, an irrigation tubing 150 may be provided to pass fluid to the distal assembly 15 from the control handle 16. In the illustrated embodiment of FIG. 2, the tubing 150 passes through the central lumen 18 of the catheter body 12, the lumen 19b of the deflectable section 14, and into the distal assembly 15.

In use, a suitable guiding sheath is inserted into the patient with its distal end positioned at a desired location. An example of a suitable guiding sheath for use in connection with the present invention is the Preface™ Braiding Guiding Sheath, commercially available from Biosense Webster, Inc. (Diamond Bar, Calif.). The distal end of the sheath is guided into one of the chamber, for example, the atria. A catheter in accordance with an embodiment of the present invention is fed through the guiding sheath until its distal end extends out of the distal end of the guiding sheath. As the catheter is fed through the guiding sheath, the distal assembly 15 is straightened to fit through the sheath. Once the distal end of the catheter is positioned at the desired location, the guiding sheath is pulled proximally, allowing the deflectable section 14 and distal assembly 15 to extend outside the sheath, and the distal assembly 17 returns to its original shape due to its shape-memory.

The user manipulating the actuator 13 on the control handle 16 actuates deflection mechanism inside the control handle 16 to draw puller wire proximal portion 28A or 28B to deflect the distal section 14 on-plane to one or the other side of the beam 30. The user may then rotate the distal assembly 15 by rotating the control handle 16 which transfers torque to the catheter body 12 and the deflectable section 14 through the transition section(s) 65. The brackets 66A and 66B to which the tubular structures 11 and 17 of the catheter body 12 and the deflectable section 14 are bonded by means of interlocking nodes formed in the perforations 68 of the brackets 66A and 66B under heat fusion.

Suitable materials for construction of the beam, the beam stiffeners and/or the half-cylindrical brackets include 50/50NiTi, titanium (Ti-6Al-4V), phosphor bronze 510, beryllium copper, monel alloy K-500 or MP35N (a non-magnetic nickel-cobalt-chromium-molybdenum alloy). Suitable materials for the puller wire include preformed, heat treated and TEFLON coated NiTi wire, monel alloy K-500 or dual VECTRAN fibers.

Suitable materials for imbedded braided mesh for the tubular structures of the catheter body and/or the deflectable section include stainless steel (304V or 316), phosphor bronze, monel K-500, PEN or other synthetic fibers that can readily bond with PEBAX or PELLETHANE extruded thermoplastics during the secondary/outer extrusion coat or layer.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A method of manufacturing a catheter, the catheter comprising:
    an elongated catheter body comprising a first tubular structure having first central lumen, a distal end and a proximal end;
    a deflectable section having a second tubular structure having a second central lumen, and a proximal end that is distal of the proximal end of the catheter body;
    a flat beam having first and second opposing surfaces, the flat beam extending through at least the second central lumen of the deflectable section, the flat beam defining a first sub-lumen and a second sub-lumen;
    a puller wire configured with first and second segments and a U-bend segment therebetween, the U-bend segment anchored to the distal end of the flat beam, the first segment extending through the first sub-lumen and through the first central lumen of the catheter body, the second segment extending through the second sub-lumen and through the first central lumen of the catheter body;
    a first compression coil surrounding a portion of the first segment extending through the catheter body, a second compression coil surrounding a portion of the second segment extending through the catheter body;
    a pair of first and second half-cylindrical brackets, the first half-cylindrical bracket being mounted on a first surface of the beam, the second half-cylindrical bracket being mounted on a second surface of the beam, the first and second half-cylindrical brackets forming a hollow body generally surrounding the beam at or near a junction between the catheter body and the deflectable section, wherein the distal end of the first tubular structure covers a proximal portion of the hollow body and a proximal end of the second tubular structure covers a distal portion of the hollow body, wherein each bracket has at least two holes, and each of the first and second tubular structures has an inner layer with at least one interlocking node extending into a respective hole in each bracket,
the method comprising:
wrapping the junction between the first and second tubular structures in one or more heat shrink tubings to form a tube assembly;
heating the one or more heat shrink tubings to recover around the junction between the first and second tubular structures; and
heating the tube assembly to reflow inner layers of the first and second tubular structures to form the interlocking nodes within the brackets.

2. A method of claim 1, further comprising removing the at least one heat shrink tubing from the junction between the first and second tubular structure.

\* \* \* \* \*